June 10, 1958 | L. A. HAGLER | Plant Pat. 1,718
NECTARINE TREE
Filed Oct. 28, 1957
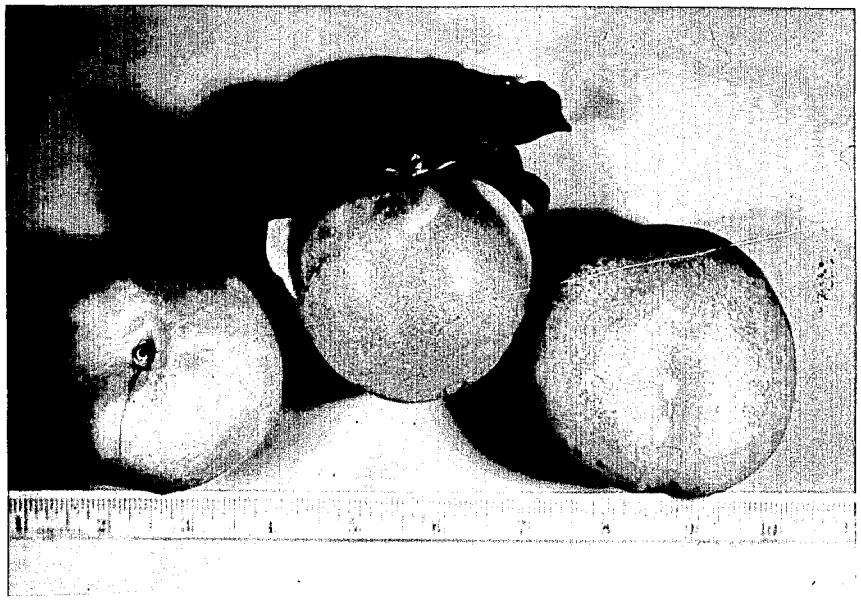
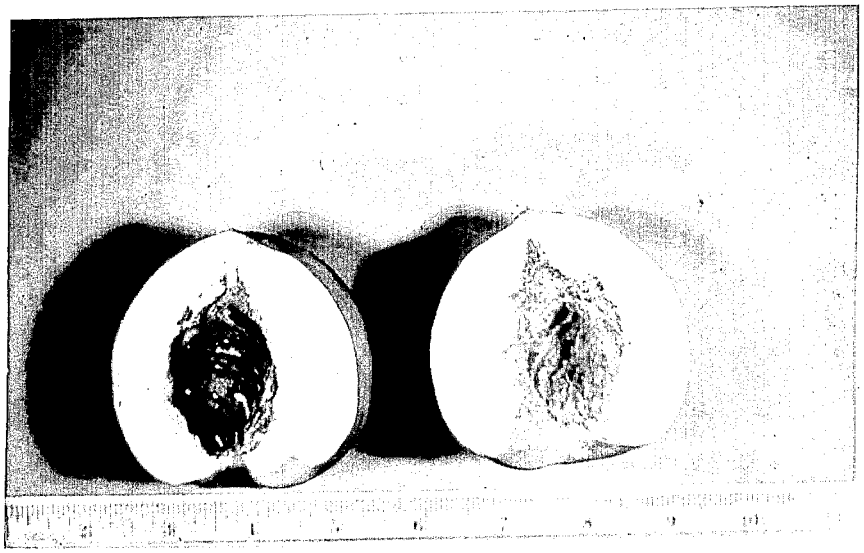
INVENTOR
L. A. Hagler
BY Robb & Robb ATTORNEYS United States Patent Office Plant Pat. 1,718
Patented June 10, 1958

1,718

NECTARINE TREE

Lisle A. Hagler, Visalia, Calif.

Application October 28, 1957, Serial No. 692,991

1 Claim. (Cl. 47—62)

The present invention relates to a new and distinct variety of nectarine tree of the yellow-fleshed freestone fruit type, which was discovered by me as a bud sport on a "Le Grand" nectarine tree in a cultivated orchard under my supervision near Visalia, Tulare County, California.

At the time of my discovery of the sport above referred to, I was supervising the picking of fruit of the "Le Grand" variety (Plant Patent No. 549) preparatory to packing the same for commercial purposes in my regular packing house, and my attention was attracted to a forked limb on one of the "Le Grand" trees which appeared to be bearing fruit which had a much higher red coloring than was normal for that variety. On closer examination and comparison of the fruit with that of the regular "Le Grand" variety, I found that the "Le Grand" tree had sported, and I thereupon took steps to promptly preserve the sport and to later asexually reproduce the same.

Continued observations of the sport, as well as asexual reproductions thereof by budding, as performed by me on my own property near Visalia, California, showed that the fruit of the new variety was definitely different from that of "Le Grand" by virtue of being of the freestone type, earlier in ripening habit by about 5 or 6 days ahead of "Le Grand," and consistently characterized by a more highly red coloring of the fruit skin. These characteristics represent a distinct advantage over other varieties from a commercial standpoint, and have been proved to be fixed and transmissible through succeeding propagations.

Although the seed or stone characteristics of the fruit of my new sport are somewhat similar to those of the variety "Sun Grand" (Plant Patent No. 974), which sometimes makes it difficult to distinguish the same from each other, it will be amply evident to experts and to others by careful comparison that the stones of my new variety are slightly wider, their pit marks are not as deep and the pit grooves are not as deep. Moreover, the new sport is definitely a freestone type of nectarine, but does not ripen as early as the variety "Sun Grand" which normally ripens more than two weeks ahead of "Le Grand."

In particular, the ripening period of the new sport, falls almost midway between that of "Sun Grand" and "Le Grand" when grown under comparable cultural conditions in the same general locality, and together with the high red coloring of the fruit of the sport, makes my new variety especially desirable and outstanding for commercial fruit production.

The acompanying drawing shows typical specimens of the fruit and foliage of my new variety, with one of the fruit specimens shown in cross-section to expose the stone in one half-section and the pit cavity in the other half-section, all as depicted in color as nearly true as it is reasonably possible to make the same in a color illustration of this character.

The following is a detailed description of my new variety, with color terminology in accordance with Maerz and Paul's Dictionary of Color, except where general color terms of ordinary dictionary significance are obvious:

Parentage: Sport of "Le Grand."

Propagation: Holds its distinguishing characteristics through succeeding propagations by budding.

Locality where grown and observed: Near Visalia, California.

Tree: Large; vigorous; open and vase-formed; very productive; regular bearer.

*Trunk.*—Medium size.

*Branches.*—Heavy; thick. Color—gray. New wood—slightly reddish green at top and light green at bottom.

*Leaves.*—Color: dorsal side—from Cypress Green, Plate 23–L–7, to Empire Green, Plate 23–E–9, with a light yellow tinge; ventral side—from Hellebore Green, Plate 23–L–3, to Cypress Green, Plate 23–L–7, with light yellow tinge. Size—from medium to large, but mostly medium; many over 5½" long by about 1½" wide; some leaves slightly curved and waved. Base angle—mostly broadly acute, but some obtuse. Apex angle—mostly broadly acute. Margin—crenate; glandular at base. Glands—from 1 to 4, but mostly 2 each per leaf; some on leaf petiole, and some on leaf base margin; globose; from small to medium size. Petiole: length—usually about ½"; thickness—about 1/16"; color: ventral side—from Russet Green, Plate 20–L–1, to Oasis Green, Plate 20–L–2; dorsal side—from Grass Green, Plate 21–L–4, to Parrot Green, Plate 21–L–6. Stipules—none.

Flowers: Self-fertile.

Fruit:

*Ripening date.*—About July 4 to July 6.

*Size.*—Mostly large.

*Axial diameter.*—About 3".

*Transverse diameter.*—About 2⅝".

*Suture diameter.*—About 2¾".

*Surface.*—Mostly regular; smooth.

*Form.*—Uniform shape; some protrusion of lips; mostly elongated to round ovate.

*Tendency to split.*—Very slight.

*Tendency to crack*—None.

*Base.*—Flat.

*Apex.*—Some rounded, but mostly flat, with small point at apex.

*Suture.*—Shallow; with very slight depression and with a slight suture stripe; suture lip slightly protruding unequally.

*Transverse section.*—Round; with slight suture bulge.

*Ventral side.*—Rounded; with uniform side.

*Cavity.*—Deep; broad; flaring; about ⅜" deep; about ¾" wide. Color—full red.

*Stem.*—Stout; heavy; short; adheres tightly to stone.

*Stem scar.*—Large; flat; slightly rounded.

*Skin.*—Thick; tough; adheres tightly to flesh.

*Pubescence.*—None.

*Color.*—Predominantly red on tree-ripe fruit; usually from light Pomegranite Red, Plate 6–L–1, to light yellowish Cardinal Red. Plate 6–L–10; some Saraband Red, Plate 9–K–7, with an under color of from Genista, Plate 9–J–8, to Orange Chrome, Plate 9–K–7.

*Flesh.*—Firm; melting; crisp. Color—Golden Yellow, Plate 10–L-7, with slight red around pit. Texture—fine. Flavor—sweet, but slightly tart. Aroma—slightly aromatic. Juice—abundant.

Fibers—short; thin; tender. Eating quality—very good.

Stone:

*Adherence to flesh.*—Free; separates freely from flesh.

*Size.*—Large. Length—about 1⅜". Width—about 1⅛". Thickness—about 13/16".

*Form.*—Obovoid.

*Base.*—Large; medium angle.

*Stem scar.*—Broad; oval; elongated.

*Apex.*—Wide.

*Sides.*—Equal.

*Dorsal edge.*—Has deep line markings.

*Ventral edge.*—Thick; with deep groove at base end.

*Ridges.*—Rounded.

*Surface.*—Irregularly pitted and furrowed.

*Color.*—Light brown, with slight red color at base end.

*Tendency to split.*—None.

Keeping quality: Good.

Shipping quality: Good.

Use: Market; dessert.

I claim:

A new and distinct variety of nectarine tree of the yellow-fleshed freestone fruit type, substantially as herein shown and described, characterized particularly as to novelty by its habit of ripening about five or six days earlier than the fruit of its parent variety "Le Grand" (Plant Patent No. 549), and by a higher red coloring of the skin of its fruit as compared with "Le Grand."

No references cited.